United States Patent
Blaisdell et al.

(10) Patent No.: US 10,639,353 B2
(45) Date of Patent: *May 5, 2020

(54) MONO- AND DI-PEG IL-10 PRODUCTION; AND USES

(71) Applicant: Merck Sharp & Dohme Corp., Rahway, NJ (US)

(72) Inventors: Steven J. Blaisdell, Jackson, NJ (US); Collette M. Cutler, Bloomingdale, NJ (US); Brittany C. Paporello, Martinsville, NJ (US); Alexandre Ambrogelly, Westfield, NJ (US)

(73) Assignee: Merck Sharp & Dohme Corp, Rahway, NJ (US)

( * ) Notice: Subject to any disclaimer, the term of this patent is extended or adjusted under 35 U.S.C. 154(b) by 53 days.

This patent is subject to a terminal disclaimer.

(21) Appl. No.: 15/393,013

(22) Filed: Dec. 28, 2016

(65) Prior Publication Data
US 2017/0202923 A1    Jul. 20, 2017

Related U.S. Application Data

(60) Continuation of application No. 14/989,068, filed on Jan. 6, 2016, now Pat. No. 9,566,345, which is a continuation of application No. 14/183,302, filed on Feb. 18, 2014, now Pat. No. 9,259,478, which is a division of application No. 13/140,390, filed as application No. PCT/US2009/068012 on Dec. 15, 2009, now Pat. No. 8,691,205.

(60) Provisional application No. 61/245,182, filed on Sep. 23, 2009, provisional application No. 61/138,421, filed on Dec. 17, 2008.

(51) Int. Cl.
| C07K 14/54 | (2006.01) |
| A61K 38/20 | (2006.01) |
| A61K 47/14 | (2017.01) |
| A61K 47/60 | (2017.01) |
| A61P 35/00 | (2006.01) |
| A61K 31/506 | (2006.01) |
| A61K 31/513 | (2006.01) |
| A61K 33/24 | (2019.01) |
| A61K 45/06 | (2006.01) |

(52) U.S. Cl.
CPC ........ *A61K 38/2066* (2013.01); *A61K 31/506* (2013.01); *A61K 31/513* (2013.01); *A61K 33/24* (2013.01); *A61K 45/06* (2013.01); *A61K 47/60* (2017.08); *A61P 35/00* (2018.01)

(58) Field of Classification Search
None
See application file for complete search history.

(56) References Cited

U.S. PATENT DOCUMENTS

| 5,624,823 A | 4/1997 | Sachs et al. |
| 5,665,345 A | 9/1997 | Yarchoan et al. |
| 5,824,784 A | 10/1998 | Kinstler et al. |
| 5,866,134 A | 2/1999 | Fine et al. |
| 5,989,867 A | 11/1999 | Knappe et al. |
| 6,217,857 B1 | 4/2001 | Mosmann et al. |
| 6,387,364 B1 | 5/2002 | Ferguson |
| 6,660,258 B1 | 12/2003 | Tovey |
| 6,770,272 B2 | 8/2004 | Strom et al. |
| 6,989,377 B2 | 1/2006 | Hayes et al. |
| 7,052,686 B2 | 5/2006 | Lee et al. |
| 7,261,882 B2 | 8/2007 | Watkins |
| 7,650,243 B2 | 1/2010 | Gantier et al. |
| 7,749,490 B2 | 7/2010 | Sommer et al. |
| 7,939,056 B2 | 5/2011 | Horwitz et al. |
| 8,691,205 B2 * | 4/2014 | Blaisdell ............ A61K 38/2066 424/78.18 |
| 9,943,568 B2 * | 4/2018 | Oft ..................... A61K 38/2066 |
| 2002/0044921 A1 | 4/2002 | Lee et al. |
| 2003/0186386 A1 | 10/2003 | Hansen et al. |
| 2005/0260767 A1 | 11/2005 | Clerici et al. |
| 2006/0046961 A1 | 3/2006 | McKay et al. |
| 2008/0058246 A1 | 3/2008 | Bhaskaran et al. |
| 2008/0069797 A1 | 3/2008 | Roncarolo et al. |
| 2008/0081031 A1 * | 4/2008 | Oft ..................... A61K 38/2066 424/85.2 |
| 2010/0068147 A1 | 3/2010 | Hibberd et al. |
| 2010/0111898 A1 | 5/2010 | Pelura |
| 2010/0297070 A1 | 11/2010 | Dugan et al. |

FOREIGN PATENT DOCUMENTS

| WO | WO 1992012725 | 8/1992 |
| WO | WO 1992012726 | 8/1992 |
| WO | 1995/03411 | 2/1995 |
| WO | WO 1995019780 | 7/1995 |
| WO | WO 1997003690 | 2/1997 |
| WO | WO 2001005821 | 1/2001 |
| WO | WO 2004044006 | 5/2004 |

(Continued)

OTHER PUBLICATIONS

Cindric, et al., (2007) "Structural 1-16 characterization of PEGylated rHuG-CSF and location of PEG attachment sites". Journal of Pharmaceutical and Biomedical Analysis. New York. NY. US, 44(2):388-395.

(Continued)

*Primary Examiner* — Joanne Hama
*Assistant Examiner* — Jegatheesan Seharaseyon
(74) *Attorney, Agent, or Firm* — Robert Brian Johnson (57) ABSTRACT

Provided are methods of producing mono- and di-pegylated IL-10.

23 Claims, 2 Drawing Sheets

(56) References Cited

FOREIGN PATENT DOCUMENTS

| WO | WO-2006094530 A1 * | 9/2006 | ........... A61K 9/0019 |
|----|----|----|----|
| WO | WO 2006119170 | 11/2006 | |

OTHER PUBLICATIONS

Schneiderheinze, J., et al., (2009) "Rapid online proteolytic mapping of PEGylated rhGH for identity confirmation. quantitation of methionine oxidation and quantitation of UnPEGylated N-terminus using HPLC with UV detection", Journal of Chromatography B: Biomedical Sciences & Applications. Elsevier. Amsterdam. NL., 877(31):4065-4070.
Muecke, Susanne, et al., (2000) "Suppression of the Tumorigenic Growth of Burkitt's Lymphoma Cells in Immunodeficient Mice by Cytokine Gene Transfer Using EBV-Derived Episomal Expression Vectors", Int. J. Cancer, 86:301-306.
Berman et al. (1996) "Systemic administration of cellular IL-10 induces an effective, specific, and long-lived immune response against established tumors in mice" *J Immunol* 157:231-238.
Cannistra & Niloff (1996) "Cancer of the uterine cervix." *New Engl J Med* 334:1030-1038.
Chen & Zlotnik (1991) "IL-10: a novel cytotoxic T cell differentiation factor" *J Immunol* 147:528-534.
Davidson & Diamond (2001) "Autoimmune diseases" *New Engl J Med* 345:340-350.
Enzinger & Mayer (2003) "Esophageal cancer" *New Engl J Med* 349:2241-2252.
Farrar et al. (1999) "Cancer dormancy. VII. A regulatory role for CD8+ T cells and IFN-gamma in establishing and maintaining the tumor-dormant state" *J Imunol* 162:2842-2849.
Fiorentino et al. (1989) "Two types of mouse T helper cell. IV. Th2 clones secrete a factor that inhibits cytokine production by Th1 clones" *J Exp Med* 170:2081-2095.
Forastiere et al. (2001) "Head and neck cancer" *New Engl J Med* 345:1890-1900.
GenBank Accession No. M37897 "Mouse interleukin 10 mRNA, complete cds" dated Apr. 27, 1993.
GenBank Accession No. NP_000563 "interleukin-10 precursor [*Homo sapiens*]" dated Mar. 3, 1995.
Groux et al. (1998) "A transgenic model to analyze the immunoregulatory role of IL-10 secreted by antigen-presenting cells" *J Immunol* 162:1723-1729.
Groux et al. (1998) "Inhibitory and stimulatory effects of IL-10 on human CD8+ T cells" *J Immunol* 160:3188-3193.
Hagenbaugh et al. (1997) "Altered immune responses in interleukin 10 transgenic mice" *J Exp Med* 185:2101-2110.
Huang et al. (1996) "Interleukin 10 Suppresses Tumor Growth and Metastasis of Human Melanoma Cells: Potential Inhibition of Angiogenesis" Clinical Cancer Research, The American Assn for Cancer Research 2(12):1969-1979.
Ishikawa et al. (2005) "Interleukin-10 plasmid DNA inhibits liver and lung metastasis of Colon 26 adenocarcinoma in mice" Proceedings of the Annual Meeting, American Association for Cancer Research 46:792-793.
Izbicki et al. (1997) "Prognostic value of immunohistochemically identifiable tumor cells in lymph nodes of patients with completely resected esophageal cancer" *New Engl J Med* 337:1188-1194.
Katre (1993) "The Conjugation of Proteins with Polyethylene Glycol and Other Polymers Altering Properties of Proteins to Enhance their Therapeutic Potential" *Advanced Drug Delivery Reviews* 10(1):91-114.
Kokura et al. (2003) "The blocking of NFkB activation by systemicinterleukin-10 gene therapy inhibits liver and lung metastasis of colon 26 adenocarcinoma in mice" Gastroenterology 124(4):A603.
Kundu et al. (1996) "Antimetastatic and antitumor activities of interleukin 10 in a murine model of breast cancer" *J Natl Cancer Inst* 88:536-541.
Kundu et al. (1997) "Interleukin-10 inhibits tumor metastasis, down regulates MHC class I, enhances NK lysis" Cellular Immunology, Academic Press 180(1):55-61.
Le et al. (2001) "Pre-existing tumor-sensitized T cells are essential for eradication of established tumors by IL-12 and cyclophosphamide plus IL-12" *J Immunol* 167:6765-6772.
Lu et al. (2004) "Prognostic factors in resected stage I non-small-cell lung cancer: a multivariate analysis of six molecular markers" *J Clin Oncol* 22:4575-4583.
Lynch & Chapelle (2003) "Hereditary colorectal cancer" *New Engl J Med* 348:919-932.
Miki et al. (2000) "Anti-metastatic effect of IL-10 gene modification in human lung cancer cells is differentially regulated by organ microenvironments" Proceedings of the Annual Meeting, American Association for Cancer Research 41:3.
Osborne (1998) "Tamoxifen in the treatment of breast cancer" *New Engl J Med* 339:1609-1618.
Ramirez-Montagut et al. (2003) "Immunity to melanoma: unraveling the relation of tumor immunity and autoimmunity" *Oncogene* 22:3180-3187.
Sakamoto et al. (2003) "Interleukin-10 gene therapy enhances antitumor effect of CPT-11 for lung metastasis of colon 26 adenocarcinoma in mice" Gastroenterology 124(4):A456.
Sawaya et al. (2003) "Risk of cervical cancer associated with extending the interval between cervical-cancer screenings" *New Engl J Med* 349:1501-1509.
Smith et al. (1996) "Administration of interleukin-10 at the time of priming protects Corynebacterium parvum-primed mice against LPS- and TNF-alpha-induced lethality" *Cellular Immunology* 173(2):207-214.
Syto et al. (1998) "Structural and biological stability of the human interleukin 10 homodimer" *Biochemistry* 37(48):16943-16951.
Von Andrian & Mackay (2000) "T-cell function and migration. Two sides of the same coin" New Engl J Med 343:1020-1034.
Zheng et al. (1996) "Interleukin-10 inhibits tumor metastasis through an NK cell-dependent mechanism" *J Exp Med* 184:579-584.

* cited by examiner

MONO- AND DI-PEG IL-10 PRODUCTION; AND USES

FIELD OF THE INVENTION

The present invention encompasses mono-pegylated (PEG) and di-PEG IL-10 compositions and methods of use.

BACKGROUND OF THE INVENTION

The cytokine interleukin-10 (IL-10) is a dimer that becomes biologically inactive upon disruption of the non-covalent interactions connecting its two monomer subunits. IL-10 was first identified as a product of the type 2 helper T cell and later shown to be produced by other cell types including B cells and macrophages. It also inhibits the synthesis of several cytokines produced from type 1 helper T cells, such as γ-interferon, IL-2, and tumor necrosis factor-α (TNF-α). The ability of IL-10 to inhibit cell-mediated immune response modulators and suppress antigen-presenting cell-dependent T cell responses demonstrates IL-10 has immunosuppressive properties. This cytokine also inhibits monocyte/macrophage production of other cytokines such as IL-1, IL-6, IL-8, granulocyte-macrophage colony-stimulating factor (GM-CSF), granulocyte colony-stimulating factor (G-CSF), and TNF-α. As a result of its pleiotropic activity, IL-10 is under investigation for numerous clinical applications, such as for treating inflammatory conditions, bacterial sepsis, enterotoxin-induced lethal shock, and autoimmune diseases, e.g., rheumatoid arthritis, allograft rejection and diabetes.

Cancers and tumors can be controlled or eradicated by the immune system. The immune system includes several types of lymphoid and myeloid cells, e.g., monocytes, macrophages, dendritic cells (DCs), eosinophils, T cells, B cells, and neutrophils. These lymphoid and myeloid cells produce secreted signaling proteins known as cytokines. The cytokines include, e.g., interleukin-10 (IL-10), interferon-gamma (IFNγ), IL-12, and IL-23. Immune response includes inflammation, i.e., the accumulation of immune cells systemically or in a particular location of the body. In response to an infective agent or foreign substance, immune cells secrete cytokines which, in turn, modulate immune cell proliferation, development, differentiation, or migration. Excessive immune response can produce pathological consequences, such as autoimmune disorders, whereas impaired immune response may result in cancer. Anti-tumor response by the immune system includes innate immunity, e.g., as mediated by macrophages, NK cells, and neutrophils, and adaptive immunity, e.g., as mediated by antigen presenting cells (APCs), T cells, and B cells (see, e.g., Abbas, et al. (eds.) (2000) *Cellular and Molecular Immunology*, W.B. Saunders Co., Philadelphia, Pa.; Oppenheim and Feldmann (eds.) (2001) *Cytokine Reference*, Academic Press, San Diego, Calif.; von Andrian and Mackay (2000) *New Engl. J. Med.* 343:1020-1034; Davidson and Diamond (2001) *New Engl. J. Med.* 345:340-350).

Methods of modulating immune response have been used in the treatment of cancers, e.g., melanoma. These methods include treatment either with cytokines such as IL-2, IL-10, IL-12, tumor necrosis factor-alpha (TNFalpha), IFNγ, granulocyte macrophage-colony stimulating factor (GM-CSF), and transforming growth factor (TGF), or with cytokine antagonists (e.g., antibodies). Interleukin-10 was first characterized as a cytokine synthesis inhibitory factor (CSIF; see, e.g., Fiorentino, et al (1989) *J. Exp. Med.* 170:2081-2095). IL-10 is a pleiotropic cytokine produced by T cells, B cells, monocytes, that can function as both an immunosuppressant and immunostimulant (see, e.g., Groux, et al. (1998) *J. Immunol.* 160:3188-3193; and Hagenbaugh, et al. (1997) *J. Exp. Med.* 185:2101-2110).

Animal models suggest that IL-10 can induce NK-cell activation and facilitate target-cell destruction in a dose-dependent manner (see, e.g., Zheng, et al. (1996) *J. Exp. Med.* 184:579-584; Kundu, et al. (1996) *J. Natl. Cancer Inst.* 88:536-541). Further studies indicate that the presence of IL-10 in the tumor microenvironment correlates with better patient survival (see, e.g., Lu, et al. (2004) *J. Clin. Oncol.* 22:4575-4583).

Because of its relatively short half life. IL-10 has been conjugated to various partners, including polyethylene glycol. Other cytokines have also been pegylated, generally via monopegylation, e.g., PEG molecules attached to a single residue on the cytokine protein. Unfortunately, monopegylation on one IL-10 subunit leads to a non-homogenous mix of dipegylated, monopegylated and nonpegylated IL-10 molecules due to subunit shuffling. Allowing a pegylation reaction to proceed to completion will also permit non-specific and multi-pegylated target proteins, thus reducing the bioactivity of these proteins. Thus a need exists to more efficiently produce correctly pegylated IL-10 with greater production yields. The present invention satisfies this need by providing methods of producing a mixture of mono- and di-pegylated IL-10.

SUMMARY OF THE INVENTION

The present invention is based upon the discovery that a controlled reaction will produce a mix of selectively pegylated mono- and di-PEG-IL-10 which in turn improves yield of final pegylated product and has comparable efficacy to other PEG-IL-10 species.

The present invention provides a method of producing a mixture of mono- and di-pegylated IL-10, wherein at least one PEG molecule is covalently attached to at least one amino acid residue of at least one subunit of IL-10, comprising: a) reacting 1 mg/ml to 12 mg/ml of IL-10 protein with an activated PEG-linker such that the IL-10 to PEG-linker ratio is 1:1 to 1:7.7, in the presence of 0.75 mM to 35 mM of a reducing agent, at a pH of about 5.0 to 7.4 and a temperature of 5° C. to 30° C., for 12-15 hours; and b) purifying the mixture of mono- and di-pegylated IL-10. In certain embodiments, the PEG-linker is selected from the group consisting of succinimidylcarbonate-PEG, PEG-butyraldehyde, PEG-pentaldehyde, PEG-amido-propionaldehyde, PEG-urethano-propioaldehyde, and PEG-propylaldehyde, the PEG-linker is from 5,000 daltons to 12,000 daltons, or the reducing agent is selected from the group consisting of borohydride, sodium cyanoborohydride, amine borane, and picoline borane. In yet another embodiment, the mixture of mono- and di-PEG is purified by chromatography selected from the group consisting of cation exchange, anion exchange, size exclusion, and hydrophobic interaction. Also encompassed is a pharmaceutical composition comprising the mono- and di-PEG-IL-10 produced by this reaction method and a pharmaceutically acceptable carrier.

The present invention encompasses a method of producing a mixture of mono- and di-pegylated IL-10, wherein at least one PEG molecule is covalently attached to at least one amino acid residue of at least one subunit of IL-10, comprising a) reacting 7.5 mg/ml of IL-10 with an activated PEG-linker such that the IL-10 to PEG-linker ratio is 1:3.5, in the presence of 25 mM of a reducing agent, at a pH of 6.3 and a temperature of 15° C., for 15 hours; and b) purifying the mixture of mono- and di-pegylated IL-10. In certain embodiments, the PEG-linker is selected from the group consisting of succinimidylcarbonate-PEG, PEG-butyraldehyde, PEG-pentaldehyde, PEG-amido-propionaldehyde, PEG-urethano-propioaldehyde, and PEG-propylaldehyde. The molecular mass of PEG comprising the PEG-linker is from 5,000 daltons to 20,000 daltons, the reducing agent is selected from the group consisting of borohydride, sodium cyanoborohydride, amine borane, and picoline borane or the mixture of mono- and di-PEG is purified by chromatography selected from the group consisting of cation exchange, anion exchange, size exclusion, and hydrophobic interaction. Also encompassed is a pharmaceutical composition comprising the mono- and di-PEG-IL-10 produced by this reaction method and a pharmaceutically acceptable carrier.

DETAILED DESCRIPTION

As used herein, including the appended claims, the singular forms of words such as "a," "an," and "the," include their corresponding plural references unless the context clearly dictates otherwise. All references cited herein are incorporated by reference to the same extent as if each individual publication, patent application, or patent, was specifically and individually indicated to be incorporated by reference.

I Definitions

"Activation," "stimulation," and "treatment," as it applies to cells or to receptors, may have the same meaning, e.g., activation, stimulation, or treatment of a cell or receptor with a ligand, unless indicated otherwise by the context or explicitly. "Ligand" encompasses natural and synthetic ligands, e.g., cytokines, cytokine variants, analogues, muteins, and binding compositions derived from antibodies. "Ligand" also encompasses small molecules, e.g., peptide mimetics of cytokines and peptide mimetics of antibodies. "Activation" can refer to cell activation as regulated by internal mechanisms as well as by external or environmental factors. "Response," e.g., of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming.

"Activity" of a molecule may describe or refer to the binding of the molecule to a ligand or to a receptor, to catalytic activity; to the ability to stimulate gene expression or cell signaling, differentiation, or maturation; to antigenic activity, to the modulation of activities of other molecules, and the like. "Activity" of a molecule may also refer to activity in modulating or maintaining cell-to-cell interactions, e.g., adhesion, or activity in maintaining a structure of a cell, e.g., cell membranes or cytoskeleton. "Activity" can also mean specific activity, e.g., [catalytic activity]/[mg protein], or [immunological activity]/[mg protein], concentration in a biological compartment, or the like. "Proliferative activity" encompasses an activity that promotes, that is necessary for, or that is specifically associated with, e.g., normal cell division, as well as cancer, tumors, dysplasia, cell transformation, metastasis, and angiogenesis.

"Administration" and "treatment," as it applies to an animal, human, experimental subject, cell, tissue, organ, or biological fluid, refers to contact of an exogenous pharmaceutical, therapeutic, diagnostic agent, compound, or composition to the animal, human, subject, cell, tissue, organ, or biological fluid. "Administration" and "treatment" can refer, e.g., to therapeutic, placebo, pharmacokinetic, diagnostic, research, and experimental methods. "Treatment of a cell" encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding composition, or by another cell. "Treatment," as it applies to a human, veterinary, or research subject, refers to therapeutic treatment, prophylactic or preventative measures, to research and diagnostic applications. "Treatment" as it applies to a human, veterinary, or research subject, or cell, tissue, or organ, encompasses contact of PEG-IL-10 to a human or animal subject, a cell, tissue, physiological compartment, or physiological fluid. "Treatment of a cell" also encompasses situations where PEG-IL-10 contacts IL-10 receptor (heterodimer of IL-10R1 and IL-10R2) e.g., in the fluid phase or colloidal phase, as well as situations where an IL-10 agonist or antagonist contacts a fluid, e.g., where the fluid is in contact with a cell or receptor, but where it has not been demonstrated that the agonist or antagonist directly contacts the cell or receptor.

"Cachexia" is a wasting syndrome involving loss of muscle (muscle wasting) and fat, resulting from a disorder in metabolism. Cachexia occurs in various cancers ("cancer cachexia"), chronic pulmonary obstructive disorder (COPD), advanced organ failure, and AIDS. Cancer cachexia is characterized by, e.g., marked weight loss, anorexia, asthenia, and anemia. Anorexia is a disorder resulting from lack of motivation to eat, e.g., food aversion (see, e.g., MacDonald, et al. (2003) *J. am. Coll. Surg.* 197:143-161; Rubin (2003) *Proc. Natl. Acad. Sci. USA* 100:5384-5389; Tisdale (2002) *Nature Reviews Cancer* 2:862-871; Argiles, et al. (2003) *Drug Discovery Today* 8:838-844; Lelli, et al. (2003) *J. Chemother.* 15:220-225; Argiles, et al. (2003) *Curr. Opin. Clin. Nutr. Metab. Care* 6:401-406).

"Conservatively modified variants of PEG-IL-10" applies to both amino acid and nucleic acid sequences. With respect to particular nucleic acid sequences, conservatively modified variants refers to those nucleic acids which encode identical or essentially identical amino acid sequences or, where the nucleic acid does not encode an amino acid sequence, to essentially identical nucleic acid sequences. Because of the degeneracy of the genetic code, a large number of functionally identical nucleic acids may encode any given protein.

As to amino acid sequences, one of skill will recognize that an individual substitution to a nucleic acid, peptide, polypeptide, or protein sequence which substitutes an amino acid or a small percentage of amino acids in the encoded sequence for a conserved amino acid is a "conservatively modified variant." Conservative substitution tables providing functionally similar amino acids are well known in the art. An example of a conservative substitution is the exchange of an amino acid in one of the following groups for another amino acid of the same group (U.S. Pat. No. 5,767,063 issued to Lee, et al.; Kyte and Doolittle (1982) *J. Mol. Biol.* 157: 105-132):

(1) Hydrophobic: Norleucine, Ile, Val, Leu, Phe, Cys, or Met;
(2) Neutral hydrophilic: Cys, Ser, Thr;
(3) Acidic: Asp, Glu;
(4) Basic: Asn, Gln, His, Lys, Arg;
(5) Residues that influence chain orientation: Gly, Pro;
(6) Aromatic: Trp, Tyr, Phe;
(7) Small amino acids: Gly, Ala, Ser.

"Effective amount" encompasses an amount sufficient to ameliorate or prevent a symptom or sign of the medical condition. Effective amount also means an amount sufficient to allow or facilitate diagnosis. An effective amount for a particular patient or veterinary subject may vary depending on factors such as the condition being treated, the overall health of the patient, the method route and dose of administration and the severity of side effects (see, e.g., U.S. Pat. No. 5,888,530 issued to Netti, et al.). An effective amount can be the maximal dose or dosing protocol that avoids significant side effects or toxic effects. The effect will result in an improvement of a diagnostic measure or parameter by at least 5%, usually by at least 10%, more usually at least 20%, most usually at least 30%, preferably at least 40%, more preferably at least 50%, most preferably at least 60%, ideally at least 70%, more ideally at least 80%, and most ideally at least 90%, where 100% is defined as the diagnostic parameter shown by a normal subject (see, e.g., Maynard, et al. (1996) *A Handbook of SOPs for Good Clinical Practice*, Interpharm Press, Boca Raton, Fla.; Dent (2001) *Good Laboratory and Good Clinical Practice*, Urch Publ., London, UK). An effective amount of PEG-IL-10 would be an amount sufficient to reduce a tumor volume, inhibit tumor growth, prevent metastasis, or increase CD8+ T cell infiltration in to the tumor site.

"Exogenous" refers to substances that are produced outside an organism, cell, or human body, depending on the context. "Endogenous" refers to substances that are produced within a cell, organism, or human body, depending on the context.

"Immune condition" or "immune disorder" encompasses, e.g., pathological inflammation, an inflammatory disorder, and an autoimmune disorder or disease. "Immune condition" also refers to infections, persistent infections, and proliferative conditions, such as cancer, tumors, and angiogenesis, including infections, tumors, and cancers that resist irradiation by the immune system. "Cancerous condition" includes, e.g., cancer, cancer cells, tumors, angiogenesis, and precancerous conditions such as dysplasia.

"Inhibitors" and "antagonists" or "activators" and "agonists" refer to inhibitory or activating molecules, respectively, e.g., for the activation of, e.g., a ligand, receptor, cofactor, gene, cell, tissue, or organ. A modulator of, e.g., a gene, a receptor, a ligand, or a cell, is a molecule that alters an activity of the gene, receptor, ligand, or cell, where activity can be activated, inhibited, or altered in its regulatory properties. The modulator may act alone, or it may use a cofactor, e.g., a protein, metal ion, or small molecule. Inhibitors are compounds that decrease, block, prevent, delay activation, inactivate, desensitize, or down regulate, e.g., a gene, protein, ligand, receptor, or cell. Activators are compounds that increase, activate, facilitate, enhance activation, sensitize, or up regulate, e.g., a gene, protein, ligand, receptor, or cell. An inhibitor may also be defined as a composition that reduces, blocks, or inactivates a constitutive activity. An "agonist" is a compound that interacts with a target to cause or promote an increase in the activation of the target. An "antagonist" is a compound that opposes the actions of an agonist. An antagonist prevents, reduces, inhibits, or neutralizes the activity of an agonist. An antagonist can also prevent, inhibit, or reduce constitutive activity of a target, e.g., a target receptor, even where there is no identified agonist.

To examine the extent of inhibition, for example, samples or assays comprising a given, e.g., protein, gene, cell, or organism, are treated with a potential activator or inhibitor and are compared to control samples without the inhibitor. Control samples, i.e., not treated with antagonist, are assigned a relative activity value of 100%. Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 25%. Activation is achieved when the activity value relative to the control is about 110%, generally at least 120%, more generally at least 140%, more generally at least 160%, often at least 180%, more often at least 2-fold, most often at least 2.5-fold, usually at least 5-fold, more usually at least 10-fold, preferably at least 20-fold, more preferably at least 40-fold, and most preferably over 40-fold higher.

Endpoints in activation or inhibition can be monitored as follows. Activation, inhibition, and response to treatment, e.g., of a cell, physiological fluid, tissue, organ, and animal or human subject, can be monitored by an endpoint. The endpoint may comprise a predetermined quantity or percentage of, e.g., an indicia of inflammation, oncogenicity, or cell degranulation or secretion, such as the release of a cytokine, toxic oxygen, or a protease. The endpoint may comprise, e.g., a predetermined quantity of ion flux or transport; cell migration; cell adhesion; cell proliferation; potential for metastasis; cell differentiation; and change in phenotype, e.g., change in expression of gene relating to inflammation, apoptosis, transformation, cell cycle, or metastasis (see, e.g., Knight (2000) *Ann. Clin. Lab. Sci.* 30:145-158; Hood and Cheresh (2002) *Nature Rev. Cancer* 2:91-100; Timme, et al. (2003) *Curr. Drug Targets* 4:251-261; Robbins and Itzkowitz (2002) *Med. Clin. North Am.* 86:1467-1495; Grady and Markowitz (2002) *Annu. Rev. Genomics Hum. Genet.* 3:101-128; Bauer, et al. (2001) *Glia* 36:235-243; Stanimirovic and Satoh (2000) *Brain Pathol.* 10:113-126).

An endpoint of inhibition is generally 75% of the control or less, preferably 50% of the control or less, more preferably 25% of the control or less, and most preferably 10% of the control or less. Generally, an endpoint of activation is at least 150% the control, preferably at least two times the control, more preferably at least four times the control, and most preferably at least 10 times the control.

A composition that is "labeled" is detectable, either directly or indirectly, by spectroscopic, photochemical, biochemical, immunochemical, isotopic, or chemical methods. For example, useful labels include $^{32}P$, $^{33}P$, $^{35}S$, $^{14}C$, $^{3}H$, $^{125}I$, stable isotopes, fluorescent dyes, electron-dense reagents, substrates, epitope tags, or enzymes, e.g., as used in enzyme-linked immunoassays, or fluorettes (see, e.g., Rozinov and Nolan (1998) *Chem. Biol.* 5:713-728).

"Ligand" refers, e.g., to a small molecule, peptide, polypeptide, and membrane associated or membrane-bound molecule, or complex thereof, that can act as an agonist or antagonist of a receptor. "Ligand" also encompasses an agent that is not an agonist or antagonist, but that can bind to the receptor without significantly influencing its biological properties, e.g., signaling or adhesion. Moreover, "ligand" includes a membrane-bound ligand that has been changed, e.g., by chemical or recombinant methods, to a soluble version of the membrane-bound ligand. By convention, where a ligand is membrane-bound on a first cell, the receptor usually occurs on a second cell. The second cell may have the same or a different identity as the first cell. A ligand or receptor may be entirely intracellular, that is, it may reside in the cytosol, nucleus, or some other intracellular compartment. The ligand or receptor may change its location, e.g., from an intracellular compartment to the outer face of the plasma membrane. The complex of a ligand and receptor is termed a "ligand receptor complex." Where a ligand and receptor are involved in a signaling pathway, the ligand occurs at an upstream position and the receptor occurs at a downstream position of the signaling pathway.

"Small molecules" are provided for the treatment of physiology and disorders of tumors and cancers. "Small molecule" is defined as a molecule with a molecular weight that is less than 10 kD, typically less than 2 kD, and preferably less than 1 kD. Small molecules include, but are not limited to, inorganic molecules, organic molecules, organic molecules containing an inorganic component, molecules comprising a radioactive atom, synthetic molecules, peptide mimetics, and antibody mimetics. As a therapeutic, a small molecule may be more permeable to cells, less susceptible to degradation, and less apt to elicit an immune response than large molecules. Small molecules, such as peptide mimetics of antibodies and cytokines, as well as small molecule toxins are described (see, e.g., Casset, et al. (2003) *Biochem. Biophys. Res. Commun.* 307:198-205; Muyldermans (2001) *J. Biotechnol.* 74:277-302; Li (2000) *Nat. Biotechnol.* 18:1251-1256; Apostolopoulos, et al. (2002) *Curr. Med. Chem.* 9:411-420; Monfardini, et al. (2002) *Curr. Pharm. Des.* 8:2185-2199; Domingues, et al. (1.999) *Nat. Struct. Biol.* 6:652-656; Sato and Sone (2003) *Biochem. J.* 371:603-608; U.S. Pat. No. 6,326,482 issued to Stewart, et al.).

A "chemotherapeutic agent" is a chemical compound useful in the treatment of cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime nitrogen mustards such as chiorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOLA® Bristol-Myers Squibb Oncology, Princeton, N.J.) and doxetaxel (Taxotere™, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; Xeloda® Roche, Switzerland; ibandronate; CPT11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and antiandrogens such as flutamide, nilutamide, bicalutamide, leuprolide, and goserelin; and pharmaceutically acceptable salts, acids or derivatives of any of the above "Specifically" or "selectively" binds, when referring to a ligand/receptor, antibody/antigen, or other binding pair, indicates a binding reaction which is determinative of the presence of the protein in a heterogeneous population of proteins and other biologics. Thus, under designated conditions, a specified ligand binds to a particular receptor and does not bind in a significant amount to other proteins present in the sample. The antibody, or binding composition derived from the antigen-binding site of an antibody, of the contemplated method binds to its antigen, or a variant or mutein thereof, with an affinity that is at least two fold greater, preferably at least ten times greater, more preferably at least 20-times greater, and most preferably at least 100-times greater than the affinity with any other antibody, or binding composition derived thereof. In a preferred embodiment the antibody will have an affinity that is greater than about $10^9$ liters/mol, as determined, e.g., by Scatchard analysis (Munsen, et al. (1980) *Analyt. Biochem.* 107:220-239).

"Interleukin-10" or "IL-10", as used herein, whether conjugated to a polyethylene glycol, or in a non-conjugated form, is a protein comprising two subunits noncovalently joined to form a homodimer. As used herein, unless otherwise indicated "interleukin-10" and "IL-10" can refer to human or mouse IL-10 (Genbank Accession Nos. NP_000563; M37897; or U.S. Pat. No. 6,217,857) which are also referred to as "hIL-10" or "mIL-10".

"Pegylated IL-10" or "PEG-IL-10" is an IL-10 molecule having one or more polyethylene glycol molecules covalently attached to one or more than one amino acid residue of the IL-10 protein via a linker, such that the attachment is stable. The terms "monopegylated IL-10" and "mono-PEG- IL-10", mean that at least one polyethylene glycol molecule is covalently attached to a single amino acid residue on one subunit of the IL-10 dimer via a linker. The terms "dipegylated IL-10" and "di-PEG-IL-10" mean that at least one PEG molecule is attached to a single residue on each subunit of the IL-10 dimer via a linker. The average molecular weight of the PEG moiety is preferably between about 5,000 and about 50,000 daltons. The method or site of PEG attachment to IL-JO is not critical, but preferably the pegylation does not alter, or only minimally alters, the activity of the biologically active molecule. Preferably, the increase in half-life is greater than any decrease in biological activity. For PEG-IL-10, biological activity is typically measured by assessing the levels of inflammatory cytokines (e.g., TNFα, IFNγ) in the serum of subjects challenged with a bacterial antigen (lipopolysaccharide, LPS) and treated with PEG-IL-10, as described in U.S. Pat. No. 7,052,686.

As used herein, "serum half-life", abbreviated "$t_{1/2}$", means elimination half-life, i.e., the time at which the serum concentration of an agent has reached one-half its initial or maximum value. The term "increased serum half-life" used herein in reference to a synthetic agent means that the synthetic agent is cleared at a slower rate than either the non-synthetic, endogenous agent or the recombinantly produced version thereof.

II. General

The present invention provides methods of producing a mixture of mono- and di-PEG. Pegylated IL-10 has been shown to be more efficacious in a tumor setting, see, e.g., US20080081031. The present invention provides a method to increase yields of pegylated IL-10 by purifying both monopegylated (at least one PEG molecule on one subunit of the IL-10 homodimer) and dipegylated (at least one PEG molecule on each subunit of the IL-10 homodimer) IL-10.

III. Polyethylene Glycol ("PEG")

Polyethylene glycol ("PEG") is a chemical moiety which has been used in the preparation of therapeutic protein products. The verb "pegylate" means to attach at least one PEG molecule to another molecule, e.g. a therapeutic protein. For example Adagen, a pegylated formulation of adenosine deaminase, is approved for treating severe combined immunodeficiency disease; pegylated superoxide dismutase has been in clinical trials for treating head injury; pegylated alpha interferon has been tested in phase I clinical trials for treating hepatitis; pegylated glucocerebrosidase and pegylated hemoglobin are reported to have been in preclinical testing. The attachment of polyethylene glycol has been shown to protect against proteolysis (see, e.g., Sada, et al., (1991) *J. Fermentation Bioengineering* 71:137-139).

In its most common form, PEG is a linear or branched polyether terminated with hydroxyl groups and having the general structure:

To couple PEG to a molecule (polypeptides, polysaccharides, polynucleotides, and small organic molecules) it is necessary to activate the PEG by preparing a derivative of the PEG having a functional group at one or both termini. The most common route for PEG conjugation of proteins has been to activate the PEG with functional groups suitable for reaction with lysine and N-terminal amino acid groups. In particular, the most common reactive groups involved in coupling of PEG to polypeptides are the alpha or epsilon amino groups of lysine.

The reaction of a pegylation linker with a protein leads to the attachment of the PEG moiety predominantly at the following sites: the alpha amino group at the N-terminus of the protein, the epsilon amino group on the side chain of lysine residues, and the imidazole group on the side chain of histidine residues. Since most recombinant protein possess a single alpha and a number of epsilon amino and imidazole groups, numerous positional isomers can be generated depending on the linker chemistry.

Two widely used first generation activated monomethoxy PEGs (mPEGs) were succinimidyl carbonate PEG (SC-PEG; see, e.g., Zalipsky, et al. (1992) *Biotechnol. Appl. Biochem* 15:100-114; and Miron and Wilcheck (1993) *Bioconjug. Chem.* 4:568-569) and benzotriazole carbonate PEG (BTC-PEG; see, e.g., Dolence, et al. U.S. Pat. No. 5,650,234), which react preferentially with lysine residues to form a carbamate linkage, but are also known to react with histidine and tyrosine residues. The linkage to histidine residues on IFNα has been shown to be a hydrolytically unstable imidazolecarbamate linkage (see, e.g., Lee and McNemar, U.S. Pat. No. 5,985,263).

Second generation PEGylation technology has been designed to avoid these unstable linkages as well as the lack of selectivity in residue reactivity. Use of a PEG-aldehyde linker targets a single site on the N-terminus of a polypeptide and/or protein subunit through reductive amination. IL-10 may be pegylated using different types of linkers and pH to arrive at a various forms of a pegylated molecule (see, e.g., U.S. Pat. Nos. 5,252,714, 5,643,575, 5,919,455, 5,932,462, 5,985,263, 7,052,686).

IV. Biological Activity of PEG-IL-10

Human IL-10 induces rapid development of neutralizing antibodies when administered to immunocompetent mice. To avoid this type of neutralization, subcutaneous administration of PEG-hIL-10 was given to mice deficient in B-cells, i.e., mice unable to mount an antibody response. Well established syngeneic tumors in these immunodeficient mice were either significantly delayed in growth or rejected completely by PEG-hIL-10. The tumor growth restriction or inhibition was dependent on both CD4 and CD8 T-cells. Upon depletion of CD8 cells, the inhibitory effect of PEG-hIL-10 was completely abrogated. Thus, PEG-hIL-10 induces CD8 mediated cytotoxic responses.

Further analysis of tumor tissue showed that PEG-IL-10 increased the infiltration of CD8+ T cells into the tumor at a level greater than that of non-pegylated IL-10. The level of inflammatory cytokine expression by the infiltrating CD8 cells was also higher with PEG-IL-10 treatment as compared to non-pegylated IL-10 treatment. Treatment of tumor patients with PEG-IL-10 should induce a significant antitumor response and confer a significant therapeutic benefit (see, e.g., An IL-10 protein used in the present invention contains an amino acid sequence that shares an observed homology of at least 75%, more preferably at least 85%, and most preferably at least 90% or more, e.g., at least 95%, with the sequence of a mature IL-10 protein, i.e., lacking any leader sequences. See, e.g., U.S. Pat. No. 6,217,857. Amino acid sequence homology, or sequence identity, is determined by optimizing residue matches and, if necessary, by introducing gaps as required. Homologous amino acid sequences are typically intended to include natural allelic, polymorphic and interspecies variations in each respective sequence. Typical homologous proteins or peptides will have from 25-100% homology (if gaps can be introduced) to 50-100% homology (if conservative substitutions are included) with the amino acid sequence of the IL-10 polypeptide. See Needleham et al., J. Mol. Biol. 48:443-453 (1970); Sankoff et al. in *Time Warps, String Edits, and Macromolecules: The*

*Theory and Practice of Sequence Comparison,* 1983, Addison-Wesley, Reading, Mass.; and software packages from IntelliGenetics, Mountain View, Calif., and the University of Wisconsin Genetics Computer Group, Madison, Wis.

The IL-10 moiety in the PEG-IL-10 conjugates can be glycosylated or may be modified with unglycosylated muteins or other analogs, including the BCRF1 (Epstein Barr Virus viral IL-10) protein. Modifications of sequences encoding IL-10 can be made using a variety of techniques, e.g., site-directed mutagenesis [Gillman et al., Gene 8:81-97 (1979); Roberts et al., Nature 328:731-734 (1987)], and can be evaluated by routine screening in a suitable assay for IL-10 activity. Modified IL-10 proteins, e.g., variants, can vary from the naturally-occurring sequence at the-primary structure level. Such modifications can be made by amino acid insertions, substitutions, deletions and fusions. IL-10 variants can be prepared with various objectives in mind, including increasing serum half-life, reducing an immune response against the IL-10, facilitating purification or preparation, decreasing conversion of IL-10 into its monomeric subunits, improving therapeutic efficacy, and lessening the severity or occurrence of side effects during therapeutic use. The amino acid sequence variants are usually predetermined variants not found in nature, although others may be post-translational variants, e.g., glycosylated variants. Any variant of IL-10 can be used in this invention provided it retains a suitable level of IL-10 activity. In the tumor context, suitable IL-10 activity would be, e.g., CD8+ T cell infiltrate into tumor sites, expression of inflammatory cytokines such as IFNγ, IL-4, IL-6, IL-10, and RANK-L, from these infiltrating cells, increased levels of TNFα or IFNγ in biological samples, IL-10 used in this invention can be derived from a mammal, e.g. human or mouse. Human IL-10 (hIL-10) is preferred for treatment of humans in need of IL-10 treatment. IL-10 used in this invention is preferably a recombinant IL-10. Methods describing the preparation of human and mouse IL-10 can be found in U.S. Pat. No. 5,231,012. Also included are naturally occurring or conservatively substituted variants of human and mouse IL-10. In another embodiment of the present invention, IL-10 can be of viral origin. The cloning and expression of a viral IL-10 from Epstein Barr virus (BCRF1 protein) is disclosed in Moore et al., Science 248:1230 (1990).

IL-10 can be obtained in a number of ways using standard techniques known in the art. e.g., isolated and purified from culture media of activated cells capable of secreting the protein (e.g., T-cells), chemically synthesized, or recombinant techniques, (see, e.g., Merrifield, Science 233:341-47 (1986); Atherton et al., *Solid Phase Peptide Synthesis, A Practical Approach,* 1989, I.R.L. Press, Oxford; U.S. Pat. No. 5,231,012 which teaches methods for the production of proteins having IL-10 activity, including recombinant and other synthetic techniques). Preferably, IL-10 protein is obtained from nucleic acids encoding the IL-10 polypeptide using recombinant techniques. Recombinant human IL-10 is also commercially available, e.g., from PeproTech, Inc., Rocky Hill, N.J.

PEG-IL-10 can be made using techniques well known in the art. Polyethylene glycol (PEG) can be synthesized as described, e.g., in Lundblad, R. L. et al. (1988) *Chemical Reagents for Protein Modification* CRC Press, Inc., vol. 1, pp. 105-125. PEG can be conjugated to IL-10 through use of a linker as described above. In certain embodiments, the PEG-IL-10 used in the invention is a mono-PEG-IL-10 in which one to nine PEG molecules are covalently attached via a linker to the alpha amino group of the amino acid residue at the N-terminus of one subunit of the IL-10 dimer.

V. Therapeutic Compositions, Methods

PEG-IL-10 can be formulated in a pharmaceutical composition comprising a therapeutically effective amount of the IL-10 and a pharmaceutical carrier. A "therapeutically effective amount" is an amount sufficient to provide the desired therapeutic result. Preferably, such amount has minimal negative side effects. The amount of PEG-IL-10 administered to treat a condition treatable with IL-10 is based on IL-10 activity of the conjugated protein, which can be determined by IL-10 activity assays known in the art. The therapeutically effective amount for a particular patient in need of such treatment can be determined by considering various factors, such as the condition treated, the overall health of the patient, method of administration, the severity of side-effects, and the like. In the tumor context, suitable IL-10 activity would be, e.g., CD8 T cell infiltrate into tumor sites, expression of inflammatory cytokines such as IFNγ, IL-4, IL-6, IL-10, and RANK-L, from these infiltrating cells, increased levels of TNFα or IFNγ in biological samples.

The therapeutically effective amount of pegylated IL-10 can range from about 0.01 to about 100 μg protein per kg of body weight per day. Preferably, the amount of pegylated IL-10 ranges from about 0.1 to 20 μg protein per kg of body weight per day, more preferably from about 0.5 to 10 μg protein per kg of body weight per day, and most preferably from about 1 to 4 μg protein per kg of body weight per day. Less frequent administration schedules can be employed using the PEG-IL-10 of the invention since this conjugated form is longer acting than IL-10. The pegylated IL-10 is formulated in purified form and substantially free of aggregates and other proteins. Preferably, PEG-IL-10 is administered by continuous infusion so that an amount in the range of about 50 to 800 μg protein is delivered per day (i.e., about 1 to 16 μg protein per kg of body weight per day PEG-IL-10). The daily infusion rate may be varied based on monitoring of side effects and blood cell counts.

To prepare pharmaceutical compositions containing mono-PEG-IL-10, a therapeutically effective amount of PEG-IL-10 is admixed with a pharmaceutically acceptable carrier or excipient. Preferably the carrier or excipient is inert. A pharmaceutical carrier can be any compatible, non-toxic substance suitable for delivering the IL-10 compositions of the invention to a patient. Examples of suitable carriers include normal saline, Ringer's solution, dextrose solution, and Hank's solution. Non-aqueous carriers such as fixed oils and ethyl oleate may also be used. A preferred carrier is 5% dextrose/saline. The carrier may contain minor amounts of additives such as substances that enhance isotonicity and chemical stability, e.g., buffers and preservatives, see, e.g., *Remington's Pharmaceutical Sciences and U.S. Pharmacopeia: National Formulary,* Mack Publishing Company, Easton, Pa. (1984). Formulations of therapeutic and diagnostic agents may be prepared by mixing with physiologically acceptable carriers, excipients, or stabilizers in the form of, e.g., lyophilized powders, slurries, aqueous solutions or suspensions (see, e.g., Hardman, et al. (2001) *Goodman and Gilman's The Pharmacological Basis of Therapeutics,* McGraw-Hill, New York, N.Y.; Gennaro (2000) *Remington: The Science and Practice of Pharmacy,* Lippincott, Williams, and Wilkins, New York, N.Y.; Avis, et al. (eds.) (1993) *Pharmaceutical Dosage Forms: Parenteral Medications,* Marcel Dekker, NY; Lieberman, et al. (eds.) (1990) *Pharmaceutical Dosage Forms: Tablets,* Marcel Dekker, NY; Lieberman, et al. (eds.) (1990) *Pharmaceutical Dosage Forms: Disperse Systems,* Marcel Dekker, NY;

Weiner and Kotkoskie (2000) *Excipient Toxicity and Safety*, Marcel Dekker. Inc., New York, N.Y.).

Compositions of the invention can be administered orally or injected into the body. Formulations for oral use can also include compounds to further protect the IL-10 from proteases in the gastrointestinal tract. Injections are usually intramuscular, subcutaneous, intradermal or intravenous. Alternatively, intra-articular injection or other routes could be used in appropriate circumstances.

When administered parenterally, pegylated IL-10 is preferably formulated in a unit dosage injectable form (solution, suspension, emulsion) in association with a pharmaceutical carrier. See, e.g., Avis et al., eds., *Pharmaceutical Dosage Forms: Parenteral Medications*, Dekker, N.Y. (1993); Lieberman et al., eds., *Pharmaceutical Dosage Forms: Tablets*, Dekker, N.Y. (1990); and Lieberman et al., eds., *Pharmaceutical Dosage Forms: Disperse Systems*, Dekker, N.Y. (1990). Alternatively, compositions of the invention may be introduced into a patient's body by implantable or injectable drug delivery system. e.g., Urquhart et al. *Ann. Rev. Pharmacol. Toxicol.* 24:199-236, (1984); Lewis, ed., *Controlled Release of Pesticides and Pharmaceuticals* Plenum Press, New York (1981); U.S. Pat. Nos. 3,773,919; 3,270,960; and the like. The pegylated IL-10 can be administered in aqueous vehicles such as water, saline or buffered vehicles with or without various additives and/or diluting agents.

An effective amount for a particular patient may vary depending on factors such as the condition being treated, the overall health of the patient, the method route and dose of administration and the severity of side affects (see, e.g., Maynard, et al. (1996) *A Handbook of SOPs for Good Clinical Practice*, Interpharm Press, Boca Raton, Fla.; Dent (2001) *Good Laboratory and Good Clinical Practice*, Urch Publ., London, UK).

Typical veterinary, experimental, or research subjects include monkeys, dogs, cats, rats, mice, rabbits, guinea pigs, horses, and humans.

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. Preferably, a biologic that will be used is derived from the same species as the animal targeted for treatment, thereby minimizing a humoral response to the reagent. Methods for co-administration or treatment with a second therapeutic agent, e.g., a cytokine, steroid, chemotherapeutic agent, antibiotic, or radiation, are well known in the art (see, e.g., Hardman, et al. (eds.) (2001) *Goodman and Gilman's The Pharmacological Basis of Therapeutics*, 10$^{th}$ ed., McGraw-Hill, New York, N.Y.; Poole and Peterson (eds.) (2001) *Pharmacotherapeutics for Advanced Practice: A Practical Approach*, Lippincott, Williams & Wilkins, Phila., Pa.; Chabner and Longo (eds.) (2001) *Cancer Chemotherapy and Biotherapy*, Lippincott, Williams & Wilkins, Phila., Pa.). An effective amount of therapeutic will decrease the symptoms, e.g., tumor size or inhibition of tumor growth, typically by at least 10%; usually by at least 20%; preferably at least about 30%; more preferably at least 40%, and most preferably by at least 50%.

VI. Uses

The present invention provides methods of treating a proliferative condition or disorder, e.g., cancer of the uterus, cervix, breast, prostate, testes, penis, gastrointestinal tract, e.g., esophagus, oropharynx, stomach, small or large intestines, colon, or rectum, kidney, renal cell, bladder, bone, bone marrow, skin, head or neck, skin, liver, gall bladder, heart, lung, pancreas, salivary gland, adrenal gland, thyroid, brain, e.g. gliomas, ganglia, central nervous system (CNS) and peripheral nervous system (PNS), and immune system, e.g., spleen or thymus. The present invention provides methods of treating, e.g., immunogenic tumors, non-immunogenic tumors, dormant tumors, virus-induced cancers, e.g., epithelial cell cancers, endothelial cell cancers, squamous cell carcinomas, papillomavirus, adenocarcinomas, lymphomas, carcinomas, melanomas, leukemias, myelomas, sarcomas, teratocarcinomas, chemically-induced cancers, metastasis, and angiogenesis. The invention also contemplates reducing tolerance to a tumor cell or cancer cell antigen, e.g., by modulating activity of a regulatory T cell (Treg) and or a CD8 T cell (see, e.g., Ramirez-Montagut, et al. (2003) *Oncogene* 22:3180-3187; Sawaya, et al. (2003) *New Engl. J. Med.* 349:1501-1509; Farrar, et al. (1999) *J. Immunol.* 162:2842-2849; Le, et al. (2001) *J. Immunol.* 167:6765-6772; Cannistra and Niloff (1996) *New Engl. J. Med.* 334:1030-1038; Osborne (1998) *New Engl. J. Med.* 339:1609-1618; Lynch and Chapelle (2003) *New Engl. J. Med.* 348:919-932; Enzinger and Mayer (2003) *New Engl. J. Med.* 349:2241-2252; Forastiere, et al. (2001) *New Engl. J. Med.* 345:1890-1900; Izbicki, et al. (1997) *New Engl. J. Med.* 337:1188-1194; Holland, et al. (eds.) (1996) *Cancer Medicine Encyclopedia of Cancer*, 4$^{th}$ ed., Academic Press, San Diego, Calif.).

In some embodiments, the present invention provides methods for treating a proliferative condition, cancer, tumor, or precancerous condition such as a dysplasia, with PEG-IL-10 and at least one additional therapeutic or diagnostic agent. The additional therapeutic agent can be, e.g., a cytokine or cytokine antagonist, such as IL-12, interferon-alpha, or anti-epidermal growth factor receptor, doxorubicin, epirubicin, an anti-folate, e.g., methotrexate or fluorouracil, irinotecan, cyclophosphamide, radiotherapy, hormone or anti-hormone therapy, e.g., androgen, estrogen, anti-estrogen, flutamide, or diethylstilbestrol, surgery, tamoxifen, ifosfamide, mitolactol, an alkylating agent, e.g., melphalan or cis-platin, etoposide, vinorelbine, vinblastine, vindesine, a glucocorticoid, a histamine receptor antagonist, an angiogenesis inhibitor, radiation, a radiation sensitizer, anthracycline, *vinca* alkaloid, taxane, e.g., paclitaxel and docetaxel, a cell cycle inhibitor, e.g., a cyclin-dependent kinase inhibitor, a monoclonal antibody against another tumor antigen, a complex of monoclonal antibody and toxin, a T cell adjuvant, bone marrow transplant, or antigen presenting cells, e.g., dendritic cell therapy. Vaccines can be provided, e.g., as a soluble protein or as a nucleic acid encoding the protein (see, e.g., Le, et al., supra; Greco and Zellefsky (eds.) (2000) *Radiotherapy of Prostate Cancer*, Harwood Academic, Amsterdam; Shapiro and Recht (2001) New Engl. J. Med. 344:1997-2008; Hortobagyi (1998) *New Engl. J. Med.* 339:974-984; Catalona (1994) *New Engl. J. Med.* 331:996-1004; Naylor and Hadden (2003) *Int. Immunopharmacol.* 3:1205-1215; The Int. Adjuvant Lung Cancer Trial Collaborative Group (2004) *New Engl. J. Med.* 350:351-360; Slamon, et al. (2001) *New Engl. J. Med.* 344:783-792; Kudelka, et al. (1998) *New Engl. J. Med.* 338:991-992; van Netten, et al. (1996) *New Engl. J. Med.* 334:920-921).

Also provided are methods of treating extramedullary hematopoiesis (EMH) of cancer. EMH is described (see, e.g., Rao, et al. (2003) *Leuk. Lymphoma* 44:715-718; Lane, et al. (2002) *J. Cutan. Pathol.* 29:608-612).

The broad scope of this invention is best understood with reference to the following examples, which are not intended to limit the inventions to the specific embodiments.

All citations herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

EXAMPLES

I. General Methods.

Standard methods in molecular biology are described (Maniatis, et al. (1982) *Molecular Cloning, A Laboratory Manual*, Cold Spring Harbor Laboratory Press, Cold Spring Harbor, N.Y.; Sambrook and Russell (2001) *Molecular Cloning*, 3$^{rd}$ ed., Cold Spring Harbor Laboratory Press, Cold Spring Harbor, N.Y.; Wu (1993) *Recombinant DNA*, Vol. 217, Academic Press, San Diego, Calif.). Standard methods also appear in Ausubel, et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science*, Vol. 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science*, Vol. 2, John Wiley and Sons, Inc., New York; Ausubel, et al. (2001) *Current Protocols in Molecular Biology*, Vol. 3, John Wiley and Sons, Inc., NY, NY, pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies is described (Coligan, et al. (2001) *Current Protocols in Immunology*, Vol. 1, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protocols in Immunology*, Vol. 4, John Wiley, Inc., New York). Methods for making PEG-IL-10 are described, e.g., in U.S. Pat. No. 7,052,686.

Methods for flow cytometry, including fluorescence activated cell sorting (FACS), are available (see, e.g., Owens, et al. (1994) *Flow Cytometry Principles for Clinical Laboratory Practice*, John Wiley and Sons, Hoboken, N.J.; Givan (2001) *Flow Cytometry*, 2$^{nd}$ ed.; Wiley-Liss, Hoboken, N.J.; Shapiro (2003) *Practical Flow Cytometry*, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probes (2003) *Catalogue*, Molecular Probes, Inc., Eugene, Oreg.; Sigma-Aldrich (2003) *Catalogue*, St. Louis, Mo.).

Standard methods of histology of the immune system are described (see, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila, Pa.; Louis, et al. (2002) *Basic Histology: Text and Atlas*, McGraw-Hill, New York, N.Y.).

Methods for the treatment and diagnosis of cancer are described (see, e.g., Alison (ed.) (2001) *The Cancer Handbook*, Grove's Dictionaries, Inc., St. Louis, Mo.; Oldham (ed.) (1998) *Principles of Cancer Biotherapy*, 3$^{rd}$. ed., Kluwer Academic Publ., Hingham, Mass.; Thompson, et al. (eds.) (2001) *Textbook of Melanoma*, Martin Dunitz, Ltd., London, UK Devita, et al. (eds.) (2001) *Cancer: Principles and Practice of Oncology*, 6$^{th}$ ed., Lippincott, Phila, Pa.; Holland, et al. (eds.) (2000) *Holland-Frei Cancer Medicine*, BC Decker, Phila., Pa.; Garrett and Sell (eds.) (1995) *Cellular Cancer Markers*, Humana Press, Totowa, N.J.; MacKie (1996) *Skin Cancer*, 2$^{nd}$ ed., Mosby, St. Louis; Moertel (1994) *New Engl. J. Med.* 330:1136-1142; Engleman (2003) *Semin. Oncol.* 30(3 Suppl. 8):23-29; Mohr, et al. (2003) *Onkologie* 26:227-233).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne, et al. (2000) *Bioinformatics* 16: 741-742; Menne, et al. (2000) *Bioinformatics Applications Note* 16:741-742; Wren, et al. (2002) *Comput. Methods Programs Biomed.* 68:177-181; von Heijne (1983) *Eur. J. Biochem.* 133:17-21; von Heijne (1986) *Nucleic Acids Res.* 14:4683-4690).

II. Pegylated IL-10

IL-10 (e.g., rodent or primate) was dialyzed against 50 mM sodium phosphate, 100 mM sodium chloride pH ranges 5-7.4. A 1:1-1:7 molar ratio of 5K PEG-propyladehyde was reacted with IL-10 at a concentration of 1-12 mg/ml in the presence of 0.75-30 mM sodium cyanoborohydride. Alternatively the reaction can be activated with picoline borane in a similar manner. The reaction was incubated at 5-30° C. for 3-24 hours.

Figure 1:
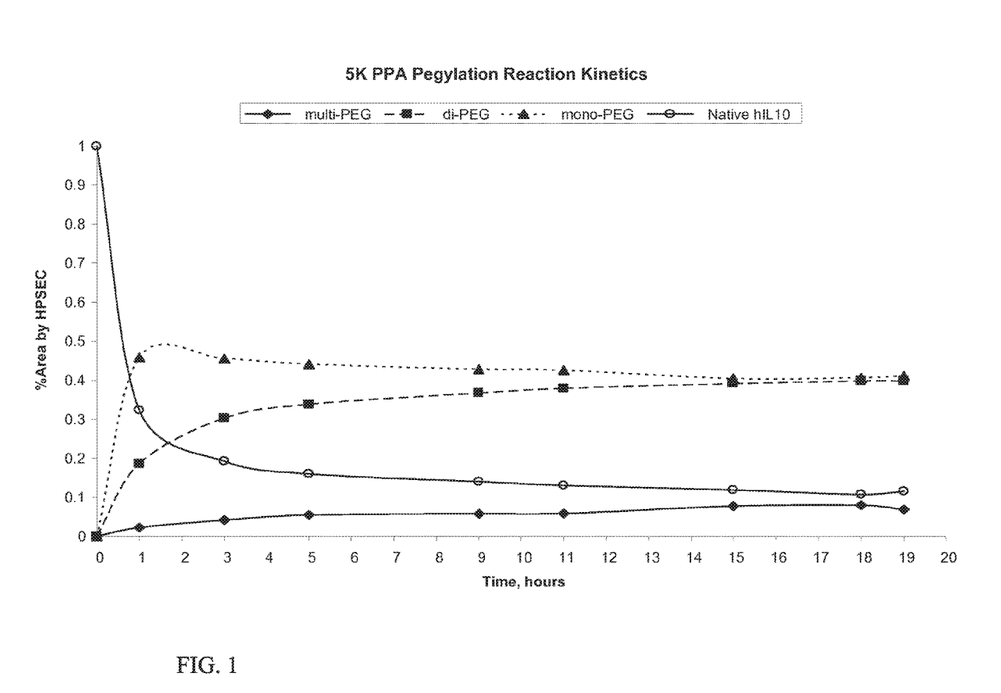
FIG. 1 shows the reaction kinetics of producing mono- and di-PEG-IL-10.

In particular, the pH of the pegylation reaction was adjusted to 6.3, 7.5 mg/ml of hIL-10 was reacted with PEG to make the ratio of IL-10 to PEG linker 1:3.5. The final concentration of cyanoborohydride was 25 mM, and the reaction was carried out at 15° C. for 12-15 hours. FIG. 1 shows the reaction kinetics of mono- and di-PEG-IL-10. The mono- and di-PEG IL-10 are the largest products of the reaction, with the concentration of each at 50% at termination.

The reaction was quenched using an amino acid such as glycine and lysine or, alternatively, Tris buffers. Multiple purification methods have been employed such as gel filtration, anion and cation exchange chromatographies, and size exclusion to isolate the desired PEGylated prototypes.

Alternatively, IL-10 is dialyzed against 10 mM sodium phosphate pH 7.0, 100 mM NaCl. The dialyzed IL-10 was diluted 3.2 times to a concentration of about 0.5 to 12 mg/ml using the dialysis buffer. Prior to the addition of the linker, SC-PEG-12K (Delmar Scientific Laboratories, Maywood, Ill.), 1 volume of 100 mM Na-tetraborate at pH 9.1 is added into 9 volumes of the diluted IL-10 to raise the pH of the IL-10 solution to 8.6. The SC-PEG-12K linker is dissolved in the dialysis buffer and the appropriate volume of the linker solution (1.8 to 3.6 mole linker per mole of IL-10) is added into the diluted IL-10 solution to start the pegylation reaction. The reaction is carried out at 5° C. in order to control the rate of the reaction. The reaction solution is mildly agitated during the pegylation reaction. When the mono-PEG-IL-10 yield as determined by size exclusion HPLC (SE-HPLC), is close to 40%, the reaction was stopped by adding IM glycine solution to a final concentration of 30 mM. The pH of the reaction solution is slowly adjusted to 7.0 using an HCl solution and the reaction is 0.2 micron filtered and stored at −80° C.

III. Efficacy Comparisons

To compare various prototypes of PEG-IL-10, 10 mice per treatment group were implanted subcutaneously with $10^6$ PDV6 squamous cell carcinomas in matrigel, into the right flank, in 100 μL volume. Once the mean tumor size reached 100 mm (approximately 2-3 weeks from implantation), treatment with the following murine PEG-IL-10 prototypes or control was started, once a day (unless specified, the linker was PPA):

| Control   | HEPES buffer                                   |
|-----------|------------------------------------------------|
| 0.2 mpk   | 2 × 5K diPEG-IL-10                             |
| 0.02 mpk  | 2 × 5K diPEG-IL-10                             |
| 0.2 mpk   | 1 × 5K monoPEG-IL-10                           |
| 0.02 mpk  | 1 × 5K monoPEG-IL-10                           |
| 0.2 mpk   | 1 × 5K monoPEG-IL-10 + 2 × 5K diPEG-IL-10      |
| 0.02 mpk  | 1 × 5K monoPEG-IL-10 + 2 × 5K diPEG-IL-10      |
| 0.2 mpk   | 1 × 12K monoPEG-IL-10 (SC linker)              |
| 0.02 mpk  | 1 × 12K monoPEG-IL-10 (SC linker)              |

Figure 2:
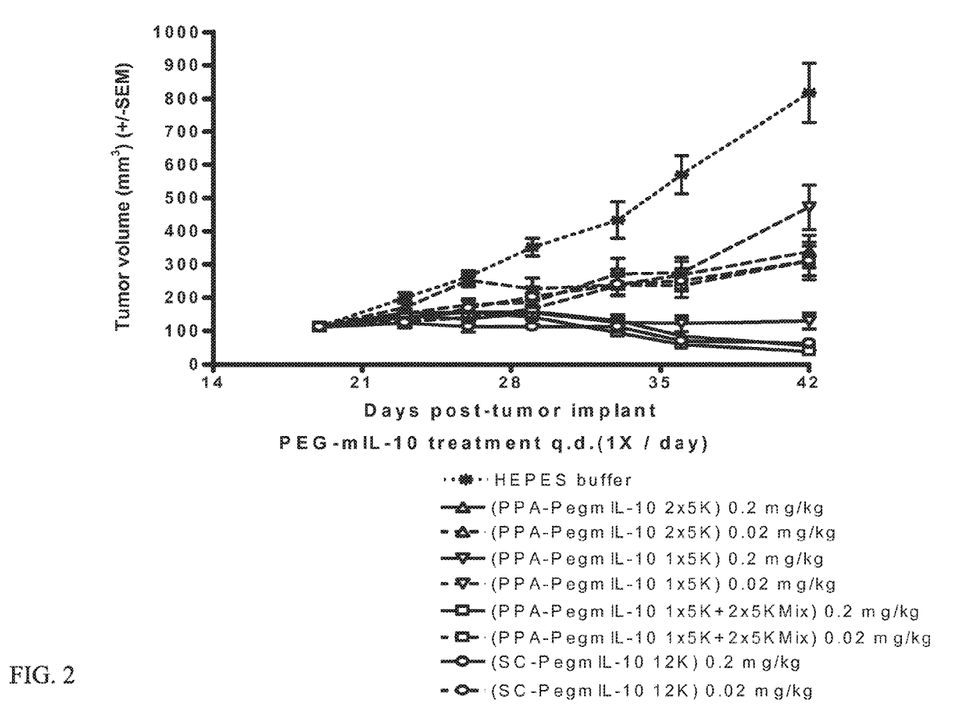
FIG. 2 shows the efficacy of various mono- and diPEG-IL-10 (murine) prototypes on implanted PDV6 squamous cell carcinomas.

The measured endpoints included tumor size (measured 2×/week), weights (measured 1×/week), and serum concentrations (measured at the start, midpoint and end of treatment). FIG. 2 shows the efficacies of the various prototypes described above.

All citations herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

What is claimed is:

1. A method of treating a patient having a proliferative condition or disorder, the method comprising:
   administering to a patient having a proliferative condition or disorder an effective amount of a composition comprising a mixture of about 50% mono-pegylated human interleukin-10 (IL-10) and about 50% di-pegylated human IL-10;
   wherein the administering is effective to treat the proliferative condition or disorder in the patient and wherein the proliferative condition or disorder is cancer; and
   wherein the PEG component of the mono-pegylated human IL-10 and di-pegylated human IL-10 is covalently attached to the alpha amino group of the amino acid residue at the N-terminus of IL-10.

2. The method of claim 1, wherein the composition is administered in an amount of from about 0.01 μg to about 100 μg per kg of body weight per day.

3. The method of claim 2, wherein the composition is administered in an amount of from about 20 μg to about 100 μg per kg of body weight per day.

4. The method of claim 2, wherein the composition is administered in an amount of from about 20 μg to about 50 μg per kg of body weight per day.

5. The method of claim 1, wherein the cancer is cancer of the uterus, cervix, breast, prostate, testes, penis, gastrointestinal tract, kidney, renal cell, bladder, bone, bone marrow, skin, head, neck, skin, liver, gall bladder, lung, pancreas, salivary gland, adrenal gland, thyroid, brain, or immune system.

6. The method of claim 5, wherein the cancer is cancer of the pancreas.

7. The method of claim 5, wherein the cancer is renal cell cancer.

8. The method of claim 5, wherein the cancer of the gastrointestinal tract is cancer of the esophagus, oropharynx, stomach, small intestine, large intestine, colon, or rectum.

9. The method of claim 8, wherein the cancer of the gastrointestinal tract is cancer of the colon or rectum.

10. The method of claim 5, wherein the cancer of the immune system is a cancer of the spleen or thymus.

11. The method of claim 1, wherein the proliferative condition or disorder is a cancer of the central nervous system (CNS) or peripheral nervous system (PNS).

12. The method of claim 11, wherein the proliferative condition or disorder is a glioma or cancer of a ganglia.

13. The method of claim 1, wherein the cancer is an epithelial cell cancer, an endothelial cell cancer, or a squamous cell carcinoma.

14. The method of claim 1, wherein the cancer is an adenocarcinoma, a lymphoma, a carcinoma, a melanoma, a leukemia, a myeloma, or a sarcoma.

15. The method of claim 1, wherein the mono-pegylated IL-10 and di-pegylated IL-10 comprise a PEG-linker selected from the group consisting of succinimidylcarbonate-PEG, PEG-butyraldehyde, PEG-pentaldehyde, PEG-amido-propionaldehyde, PEG-urethano-propioaldehyde, and PEG-propylaldehyde.

16. The method of claim 15, wherein the PEG-linker is PEG-propylaldehyde.

17. The method of claim 1, wherein the mono-pegylated IL-10 and di-pegylated IL-10 comprise a polyethylene glycol (PEG) having a molecular mass of from about 5,000 daltons to about 20,000 daltons.

18. The method of claim 1, wherein the PEG has a molecular mass of about 5,000 daltons.

19. The method of claim 1, wherein the method comprises administering at least one additional therapeutic agent.

20. The method of claim 19, wherein the at least one additional therapeutic agent is selected from the group consisting of doxorubicin, epirubicin, an anti-folate agent, irinotecan, cyclophosphamide, androgen, estrogen, anti-estrogen, flutamide, diethylstilbestrol, tamoxifen, ifosfamide, mitolactol, an alkylating agent, etoposide, vinorelbine, vinblastine, vindesine, a glucocorticoid, a histamine receptor antagonist, an angiogenesis inhibitor, radiation, a radiation sensitizer, anthracycline, a vinca alkaloid, a taxane, paclitaxel, docetaxel, a cell cycle inhibitor, or a monoclonal antibody against a tumor antigen.

21. The method of claim 20, wherein the anti-folate agent is methotrexate or fluorouracil.

22. The method of claim 20, wherein the alkylating agent is melphalan or cis-platin.

23. The method of claim 20, wherein the cell cycle inhibitor is a cyclin-dependent kinase inhibitor.

* * * * *